United States Patent [19]

Fitzpatrick

[11] Patent Number: 5,786,898
[45] Date of Patent: Jul. 28, 1998

[54] STRUCTURE AND METHOD FOR CENTRIFUGAL SEDIMENTATION PARTICLE SIZE ANALYSIS OF PARTICLES OF LOWER DENSITY THAN THEIR SUSPENSION MEDIUM

[76] Inventor: Stephen T. Fitzpatrick, R.F.D. 3 Box 90A, Gorham, Me. 04038

[21] Appl. No.: 697,435

[21] Appl. No.:

[22] Filed: Aug. 23, 1996

[22] Filed:

[51] Int. Cl.$^6$ .............. G01N 21/84; G01N 9/30; B04B 15/00
[52] U.S. Cl. .............. 356/426; 210/789; 210/515; 494/10; 422/72
[58] Field of Search .............. 494/10, 16, 17, 494/18, 20; 210/782, 788, 789, 516, 515, 518; 422/72; 356/426, 427

[56] References Cited

U.S. PATENT DOCUMENTS

| | | | |
|---|---|---|---|
| 4,478,073 | 10/1984 | Holsworth et al. | 73/61.4 |
| 4,699,015 | 10/1987 | Puhk | 73/865.5 |
| 4,772,254 | 9/1988 | Grassl et al. | 494/10 |
| 5,308,506 | 5/1994 | McEwen et al. | 210/789 |

*Primary Examiner*—Georgia Y. Epps
*Assistant Examiner*—Zandra U. Smith
*Attorney, Agent, or Firm*—William Nitkin

[57] ABSTRACT

A method and structure for analysis of the size and/or distribution of low-density particles by centrifugal sedimentation in a centrifuge chamber containing a fluid where the particles to be tested are delivered to the bottom of the centrifuge chamber and allowed to float upwards in the higher density fluid within the centrifuge chamber to be analyzed.

6 Claims, 9 Drawing Sheets

STRUCTURE AND METHOD FOR CENTRIFUGAL SEDIMENTATION PARTICLE SIZE ANALYSIS OF PARTICLES OF LOWER DENSITY THAN THEIR SUSPENSION MEDIUM

BACKGROUND OF THE INVENTION

1. Field of the Invention

This invention relates to the measurement of particle size distributions using centrifugal sedimentation and more particularly relates to the measurement of particle size distributions using density gradient stabilized sedimentation whereby microscopic and submicroscopic particles that are lower in density than the fluid in which they are suspended can be accurately analyzed using the differential sedimentation structure and method of this invention.

2. Description of the Prior Art

Centrifugal sedimentation of particles suspended in a fluid is a well-known method of measuring the size distribution of particles in the range of 0.015 micron–30 microns in diameter. The sedimentation velocity of any particle can be calculated if the particle density, fluid density, fluid viscosity, and centrifugal acceleration are known using the well-known Stokes' Equation. There are two conventional techniques for such analysis. The first is integral or homogenous sedimentation, and the second is differential or two-layer sedimentation.

In integral sedimentation a uniform suspension of particles, with an unknown size distribution, is placed in a centrifugal field at the start of the analysis. The centrifugal field causes the particles to sediment at rates which depend upon the sizes of the particles, the difference between the density of the particles and the density of the fluid medium in which they are suspended, and the viscosity of the suspending fluid. Large particles sediment at higher velocities than smaller particles. The concentration of particles remaining in the suspension is measured during the analysis usually with a light beam or x-ray beam that passes through the centrifuge. Integral sedimentation analysis utilizes such beams to determine changes in turbidity of the fluid as the sedimentation proceeds to calculate the distribution of particle sizes. The distribution of particle sizes is determined by measuring the rate at which particles sediment out of the initial suspension. In most instruments the centrifuge is optically clear or has one or more optically clear sections for the beam to pass through the sample. X-ray beams can directly measure the concentration of particles in the centrifuge. The data from the instrument is an integral or cumulative representation of the particle size distribution date which may be converted to a differential size distribution by calculating the first derivative of the cumulative distribution. Integral sedimentation may be used with particles of any density so long as the densities of the particles are different from the density of the suspending fluid. Particles that are lower in density than the density of the suspending fluid will sediment toward the surface of the fluid, that is, they will float while particles higher in density than the density of the fluid will sediment toward the bottom of the fluid, that is, they will sink.

The integral sedimentation process has many problems. First, the integral sedimentation method normally requires that the centrifuge be stopped, emptied, and cleaned after each analysis. This process makes the operation of the instrument labor intensive and makes automation of any of the integral sedimentation method processes difficult and expensive. Second, the resolution of the integral sedimentation method is limited by the physical requirements of the method. The sample may be placed in a centrifuge that is not spinning and then is accelerated to full speed, or the sample may be added to the centrifuge that is already spinning at full speed. In either case the initial conditions are not stable and well defined, and some loss of resolution may be inevitable. Unstable initial conditions are especially a problem when the particles are large enough to sediment rapidly, for example, within a few seconds. The time required for the initial conditions to stabilize may be comparable to the time for the largest particles to sediment out of the sample. Thirdly, the accuracy of the analysis can be easily compromised by convective currents within the centrifuge. Any change in temperature during the analysis will cause convection in the fluids inside the centrifuge which occurrence can cause incorrect results. Convective currents in the centrifuge must be eliminated by maintaining a constant temperature during the analysis. High-speed centrifuges, though, normally produce significant amounts of frictional heat so that special cooling of the centrifuge is required to obtain accurate results.

The second, more commonly used technique is differential sedimentation. In this method a very small sample of particles in the form of a dispersion is placed on the surface of a fluid that is inside a spinning centrifuge. The sample volume is normally very small compared to the volume of the fluid in the centrifuge so that the particles begin sedimentation as a very thin layer at the surface of the fluid in the centrifuge. If the conditions of sedimentation are stable, the individual particles settle through the fluid according to Stokes' Equation. A light beam or x-ray beam passes through the centrifuge at some distance below the surface of the fluid and measures the concentration of particles as they settle. The time required for particles to reach the detecting beam depends upon the speed and geometry of the centrifuge, the difference in density between the particles and the fluid, the viscosity of the fluid, and the diameter of the particles. The data collected using the differential sedimentation technique yields a differential particle size distribution of the sample. The particles sediment at velocities dependent upon their size until reaching the detector beam that is positioned at a known distance below the fluid's surface. The concentration of particles in the path of the detector beam is initially zero and changes during the analysis depending upon the distribution of particle sizes in the sample. All the particles start sedimentation at the same height above the detector beam and at the same time. The particles' size can be calculated from their arrival time at the detector. The result of the analysis is a differential particle size distribution. An integral distribution may be generated by integrating the differential distribution with respect to particle size. In actual practice the differential method requires a slight density gradient in the fluid inside the centrifuge to assure stable sedimentation and that no instability develops during sedimentation. The undesired instability is sometimes called "streaming." In the absence of a density gradient, streaming may occur which is the settling of the sample as a bulk fluid rather than as individual particles. Streaming can be more of a problem with higher sample concentrations and with higher particle densities so that if the net density of the fluid that contains the sample, that is the particles plus the fluid, is greater than the density of the fluid that is immediately therebelow, then the sedimentation process becomes unstable. Stability is assured if the following conditions are satisfied:

$$\frac{\delta_\rho}{\delta R} \geq 0$$

where P is the net fluid density including particles; and R is the distance from the center of rotation. Differential sedimentation can be stable if there is a continuous increase in density from the surface of the fluid to the bottom. The steepness of the gradient is normally very low, typically in the range of 0.01 g/ml per centimeter of fluid height or less although steeper gradients may be used. The effect of the density gradient on sedimentation speed is small when the particles are significantly more dense than the fluid. The presence of a density gradient helps eliminate thermal convection in the fluid within the centrifuge so that constant temperature is not required for stable sedimentation. The use of a density gradient to stabilize sedimentation in the differential method has been known for many years, and methods to produce density gradients within centrifuges are well known to those skilled in the art. The materials used to create a density gradient depend upon the nature of the particles to be analyzed and the fluid in which the sedimentation will be conducted. Samples can be prepared for analysis by dilution to a low concentration in a fluid that is lower in density than the density of the fluid at the top of the centrifuge column. This low fluid density in the diluted sample allows the sample to initially "float" on the fluid surface, and makes the sample form a very thin band of particles. The resolution of the analysis is best when the sample starts sedimentation as an extremely thin band as all the particles in the sample begin sedimentation at the same height above the detector beam. The dilution of the sample in a fluid of lower density causes the sample to spread over the surface of the fluid in the centrifuge, allowing for a thin band of particles to be created with the advantage of having the particles at the beginning of the analysis all being at the same distance from the detector beam. A suitable density gradient can be produced manually by sequential addition of fluids to the centrifuge in order of decreasing density or by an automatic gradient-producing machine. If the diluted sample is not significantly lower in density than the density of the surface of the fluid in the centrifuge, then there will be more mixing of the sample at the surface of the fluid when the sample is injected thereon, causing a loss of resolution and a less accurate test result.

One advantage of the differential sedimentation method is that there is no need to stop the centrifuge at the end of each analysis so that many samples can be run in series. The operation of the centrifuge is therefore both simpler and less labor-intensive, allowing automation of the instrument to be more easily accomplished. The maximum continuous centrifuge run time and maximum number of consecutively run samples are normally limited only by diffusion degradation of the density gradient. Often, continuous operation of a centrifuge for 4–8 hours is possible. Since the centrifuge runs continuously, the conditions within the centrifuge can be well defined and stable. This stability of operating conditions improves the accuracy and repeatability of the differential method compared to the integral method, especially when testing large particles. The differential sedimentation method, though, has one major limitation. The particles to be analyzed must be more dense than the density of the fluid through which they settle. If the particles are lower in density than the density of the fluid, they will float on the surface. This requirement makes analysis of such low-density particles in an aqueous dispersion very difficult and sometimes impossible. While it is possible in some cases to select a fluid of lower density in which to run an analysis, the choice of fluid is often limited by the nature of the particles to be analyzed and the fluid in which they are suspended. In many cases low-density particles are suspended in water and are not compatible with other fluids of low density. In such a situation one cannot use the differential sedimentation method for analysis. Thus, many low-density materials can only be measured using the integral sedimentation method described above. Examples of difficult particles to analyze include oil emulsions in water, wax emulsions in water, fat emulsions in water, polybutadiene latexes, styrene butadiene co-polymer latexes, nitrile rubber latexes, natural rubber latexes, liposomes, vinyl acetate-ethylene copolymer latexes, ground polyethylene powders, acrylic adhesive latexes, and many others. While some suitable liquids with sufficiently low densities have been found to analyze some low-density samples, for example, mixtures of methanol with water which are useful for testing samples of polymer latexes with particle densities near 1.0 g/ml, many low-density samples cannot be tested as they are not compatible with lower density liquids. Due to the difficulties of measuring low-density particles, it is common for low-density samples to be measured using some other analysis method, such as laser light scattering or homogenous centrifugal sedimentation. These alternative methods have substantial disadvantages when compared to density gradient stabilized differential sedimentation methods. Laser light scattering can measure virtually any type of sample, but the results of the analysis are normally of very low resolution. Laser light scattering measurements cannot resolve two or more closely spaced peaks in a distribution, while density gradient stabilized differential sedimentation can easily resolve multiple peaks that are less than 10% different in size.

Low-density samples can be measured using the homogenous centrifugal sedimentation method where a dilute homogenous dispersion of the sample is placed in the centrifuge chamber at the start of the analysis. There is no need for a density gradient because the fluid density is completely uniform at the start of the analysis so that the sedimentation is inherently stable. Particles in the dispersion gradually sediment out of the dispersion, either upwards toward the center of rotation when the particle density is less than that of the fluid, or downwards away from the center of rotation when the particles are more dense than the fluid. The concentration of the particles remaining in the dispersion is measured by a beam that passes through the centrifuge chamber, and the resulting distribution is an "integral form of the distribution," as discussed above.

The design of the centrifuge in which to accomplish the above processes varies depending upon the manufacturer but the most common design is based on a rotating hollow disc driven by a motor which can be set to run at a wide range of speeds so that a wide range of particles can be measured with the same instrument. Prepared samples are injected into the center of the rotating disc at the start of the analysis. The rotation of the disc carries the samples to the surface of the fluid contained within a chamber in the disc. A detector, such as a light beam or x-ray beam, passes laterally through the disc to measure the particle concentration.

SUMMARY OF THE INVENTION

It is an object of this invention to utilize density gradient stabilized differential sedimentation (DGSDS) to include an analysis of low-density particles, that is, particles that are lower in density than the density of the fluid in which they are suspended, while at the same time maintaining the advantages of the DGSDS method.

It is a further object of this invention to provide a structure and disclose a method whereby the samples of the low-density particles are placed at the bottom of the fluid in a spinning centrifuge to be accurately analyzed for particle size distribution. The particles to be tested are lower in density than the density of the fluid in the centrifuge so that the particles have a net buoyancy in the fluid. Further, the fluid in which the sample is initially suspended is miscible with the fluid in the centrifuge. In most cases the fluid in the centrifuge will contain a slight density gradient of sufficient steepness to eliminate streaming of the sample during the analysis.

It is a further object of this invention to deliver the sample to the bottom of the centrifuge in a way that does not significantly disrupt any density gradient in the centrifuge.

The basic structure of the invention involves a centrifuge chamber that can be filled with fluid of at least two or more components, with the concentrations of the components adjusted so that there is at least a slight density gradient in the fluid. The sample to be measured is prepared so while the density of the particles is at least 0.02 gm/ml lower than the density of the fluid in the centrifuge, the overall density of the sample and its suspension fluid is at least slightly higher than the highest density fluid at the bottom of the centrifuge chamber. The sample to be measured is then at the start of the analysis deposited at or near the bottom of the centrifuge chamber, that is, at the point furthest away from the center of rotation. The particles move from the bottom of the chamber toward the top during the analysis. The distribution data is collected using the traditional light beam or x-ray beam that passes through the centrifuge at a known distance from the bottom of the centrifuge chamber where the beam intensity is reduced by the presence of particles in the path of the beam. By using the method of this invention the particles in the sample float toward the top of the fluid in the chamber following Stokes' Law with a net buoyancy depending on the difference in density between the particles and the fluid in the centrifuge. The distribution data is collected and calculated in the same way as with the conventional density gradient stabilized differential sedimentation method.

While the preferred embodiment of this invention utilizes a conventional, hollow disc centrifuge chamber with modifications to allow the deposit of the sample to be tested at the bottom of the chamber, the invention is not limited to any particular instrument design and may be applied successfully to virtually any type of centrifuge. The process of this invention can measure particles of low density with very high resolution and with very little variation in results from replicate analyses. This method was specifically developed for aqueous dispersions of particles with densities near or below 1.0 g/cc, but the method can be applied to any combination of particles and fluid where the particles are lower in density than the density of the fluid in the centrifuge.

To implement the method of this invention, a centrifuge such as one of the hollow-disk design can have a V-shaped groove machined into the front face thereof and four or more small channels drilled radially from the base of the V-shaped groove, such channels connecting with the bottom of the centrifuge chamber. The level of the base of the V-shaped groove is at least slightly above the level of the fluid in the centrifuge, that is, a lesser distance from the center of rotation to keep the groove free of fluid. A sample is injected into the groove at the start of the analysis. A typical injection volume can be in the range of 20–50 microliters. When a sample is injected into the V-shaped groove, it is quickly carried by the centrifugal force to the bottom of the centrifuge chamber via the small radial channels. The combined volume of the channels can be less than 10 microliters so that even a small sample volume is sufficient to displace any liquid in the channels. Any sample that remains in the channels may be flushed to the bottom of the centrifuge by immediately following the sample with a small volume, such as 10–20 microliters of the same fluid that was used to prepare the sample for injection. As the density of the fluid at the bottom of the centrifuge chamber is lower than the density of the fluid in the sample preparation, the dispersion of particles quickly spreads to form a thin layer at the bottom of the chamber. The sedimentation of the particles proceeds in a normal fashion except that the particles move toward the surface of the fluid rather than toward the bottom of the centrifuge chamber. Multiple analyses can be run without stopping the centrifuge, and it is even possible to alternate analyses between samples that are higher in density than the density of the fluid in the centrifuge by injecting such high-density samples onto the surface of the fluid in the centrifuge while samples that are lower in density than the density of the fluid in the centrifuge are injected into the V-shaped groove and directed to the bottom of the centrifuge chamber.

BRIEF DESCRIPTION OF THE DRAWINGS

FIG. 5b illustrates a side cross-sectional view of the centrifuge of FIG. 5a.

DESCRIPTION OF THE PREFERRED EMBODIMENT(S)

Figure 1:
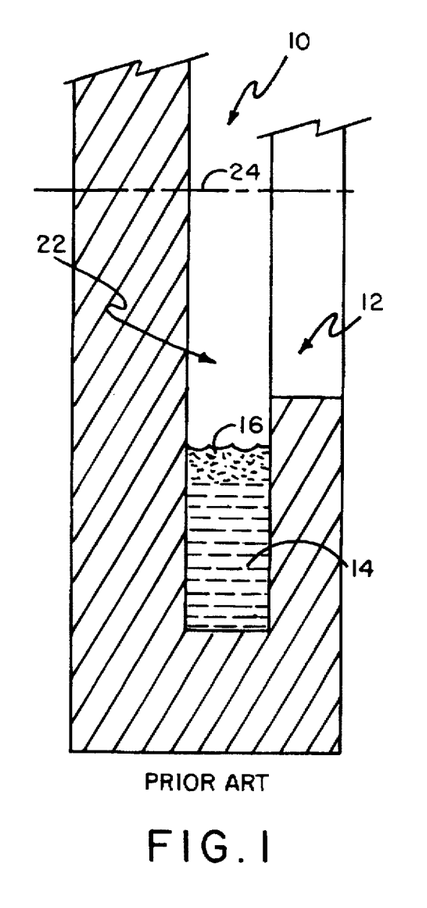
FIG. 1 illustrates a side cross-sectional view of a section of a hollow-disk centrifuge chamber of the prior art.

FIG. 1 illustrates a section of a cross-sectional view of a prior art hollow-disc centrifuge 10 rotating around its axis of rotation 24 having a chamber 22 therein for receipt of a fluid 14 and a sample 16 which are entered through opening 12 in the front of the hollow-disc centrifuge.

Figure 2:
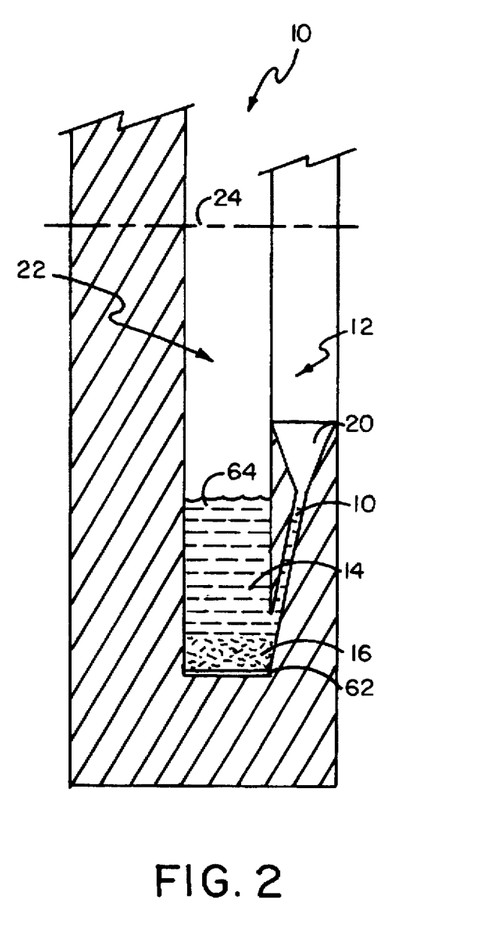
FIG. 2 illustrates a side cross-sectional view of a section of a hollow-disc centrifuge chamber embodying the structure of this invention necessary to deposit the sample to be tested at the bottom of the centrifuge chamber.

FIG. 2 illustrates a similar view of a hollow-disc centrifuge embodying the structure of this invention wherein within opening 12 is disposed a V-shaped groove 20 cut into the body of the centrifuge disc having a channel 18 leading to bottom 62 of chamber 22 wherein the sample 16 is then deposited at the bottom 62 of fluid 14 so that the particles in sample 16 then move upwards from bottom 62 to top 64 of fluid 14 in chamber 22.

Figure 3:
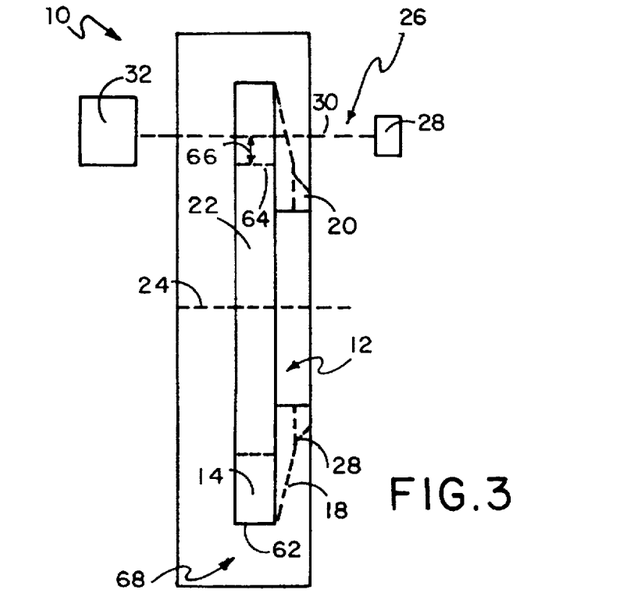
FIG. 3 illustrates a side cross-sectional view through a hollow-disc centrifuge chamber embodying the structure of this invention.
Figure 4:
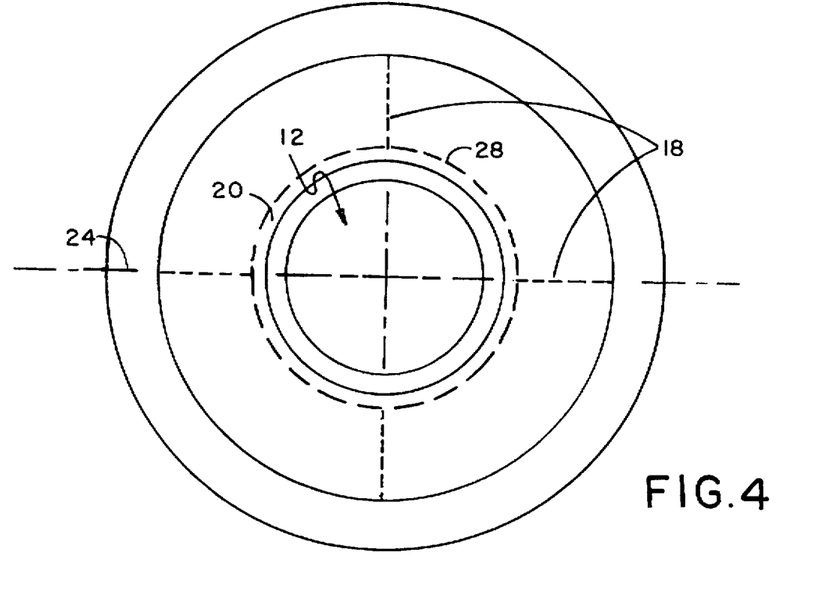
FIG. 4 illustrates a front view of the hollow-disc centrifuge chamber of FIG. 3.
Figure 6:
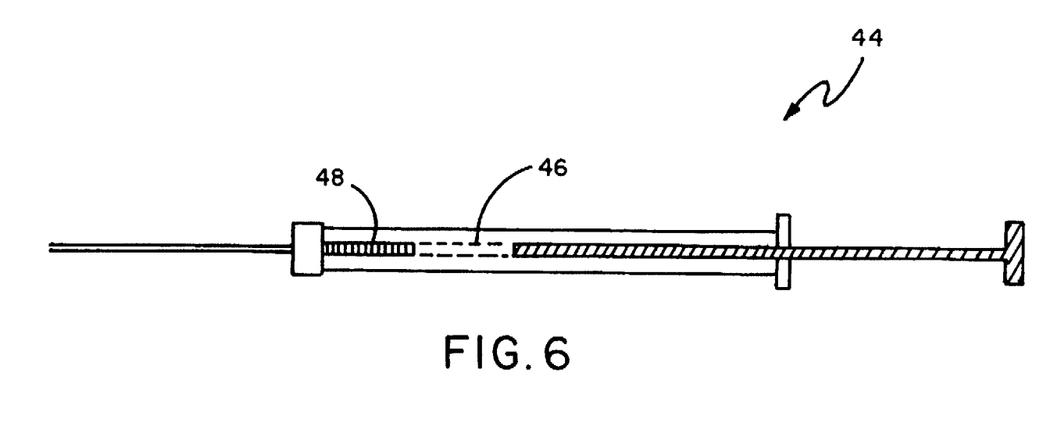
FIG. 6 illustrates a side view of a syringe prepared for sample injection.

FIG. 3 illustrates a full side view of the hollow-disc structure of FIG. 2 showing that V-shaped groove 20 runs completely around opening 12 and detectors 32 and 28 are positioned a known distance 66 from top 64 of fluid 14 within chamber 22. The disc of this invention can be machined from a solid piece of polymethylmethacrilate. The modification to the basic prior art design allows for the addition of the sample in two areas: first they can be deposited in the traditional center of disc 12 for particles that are more dense than the density of the fluid; or for particles that are of less density than the density of the fluid, they can be deposited in V-shaped groove 20 that has been machined into the face of the disc around opening 12. Base 28 of the V-shaped groove is connected to outside edge 68 of centrifuge chamber 10 by four small-diameter channels 18, as seen in dotted lines in FIG. 4. Centrifugal force carries any injected sample placed within V-shaped groove 20 down these small channels 18 to bottom 62 of the centrifuge chamber 22 where sedimentation then begins in the fluid. A greater or lesser number of channels 18 can be utilized. The V-shaped groove can accept samples that are injected by a syringe needle combination as illustrated in FIG. 6, and the centrifugal force carries the sample down the four channels 18 and deposits the sample at bottom 62, being adjacent to the outer edge 68 of chamber 22. During normal operation, the liquid level within the four capillary channels 18 is approximately equal to the liquid level in the centrifuge chamber, with any differences in level only due to slight differences in liquid density as the liquid level in each channel 18 is in equilibrium with the fluid level in the centrifuge chamber. When the sample is added in V-shaped groove 20, the liquid level in the channels increases and the liquid sample flows down channels 18 to re-establish level equilibrium with fluid 14 in centrifuge chamber 22. The total volume of the four capillary channels illustrated can be quite small, for example, 5–10 microliters or less, so that even relatively small samples, for example, 20–40 microliters, can easily displace the total volume of the channels several times. Any residual sample, for example 5–10 microliters or less in the channels may be flushed out of the channels by following the sample immediately with a small volume of clean fluid that has approximately the same composition as the sample dispersion medium but without any particles. This step can be done more easily by filling injection syringe 44, as seen in FIG. 6, with a clean fluid 46 first and then with the sample 48. As the injection is made, clean fluid 46 enters V-shaped groove 20 after sample 48 and serves to flush nearly all of the residual particles of the sample out of capillary channels 18. In this way cross-contamination of samples is substantially eliminated. Each sample 16 that is injected into V-shaped groove 20 has an overall density (liquid plus particles) that is at least slightly higher than the density of the liquid near outside edge 68 of the centrifuge chamber. When the sample reaches bottom of the centrifuge chamber 62, it rapidly spreads along bottom 62 of chamber 22 due to its higher overall density. This spreading is very much like the spreading of a low-density liquid on the surface of the fluid in a chamber and serves the same purpose. The particles in the sample begin sedimentation as a thin band at bottom 62 of chamber 22 and rise toward top 64 of fluid 14 in chamber 22. Many samples can be injected into the V-shaped groove without significantly changing the density or viscosity of the fluid in the disc because the chamber's volume is much larger than the sample size, for example, 22,000 microliters vs 30 microliters and because the composition of the sample fluid is normally not very different from the composition of the fluid at bottom 62 of the centrifuge chamber.

EXAMPLE 1

The disc shown in FIG. 3 was set to run at a constant speed of 8,600 RPM, and a density gradient was established by injecting 2.5 ml of each of the following solutions into the center of the spinning disc in the order listed (all compositions are by weight):

4.0% sucrose and 0.025% sodium laurylsulfate in Deuterium Oxide 3.5% sucrose and 0.025% sodium laurylsulfate in Deuterium Oxide 3.0% sucrose and 0.025% sodium laurylsulfate in Deuterium Oxide 2.5% sucrose and 0.025% sodium laurylsulfate in Deuterium Oxide 2.0% sucrose and 0.025% sodium laurylsulfate in Deuterium Oxide 2.5% sucrose and 0.025% sodium laurylsulfate in Deuterium Oxide 2.0% sucrose and 0.025% sodium laurylsulfate in Deuterium Oxide 1.5% sucrose and 0.025% sodium laurylsulfate in Deuterium Oxide 1.0% sucrose and 0.025% sodium laurylsulfate in Deuterium Oxide 0.5% sucrose and 0.025% sodium laurylsulfate in Deuterium Oxide 0.025% sodium laurylsulfate in Deuterium Oxide The deuterium oxide used to form the above solutions was >99.9% pure, although a somewhat lower purity deuterium oxide would also have functioned well. After all the above solutions were in the centrifuge, 1 ml of low viscosity mineral oil (USP grade) was added to retard evaporation of deuterium oxide from the surface of the fluid in the disc.

The following solution was prepared to dilute samples:

| Deuterium Oxide | 93.9% |
| Sucrose | 6.0% |
| Sodium lauryl sulfate | 0.1% |

A sample of partially agglomerated styrene butadiene copolymer latex (40% solid content, 55% by weight styrene, particle density 0.98 g/ml) was prepared for injection by dilution in the above 6% sucrose solution to give a particle concentration of approximately 0.5% by weight. A 100 microliter syringe was filled with 20 microliters of 6% sucrose in deuterium oxide (same as used for sample dilution), followed 20 microliters of the diluted sample.

Figure 7:
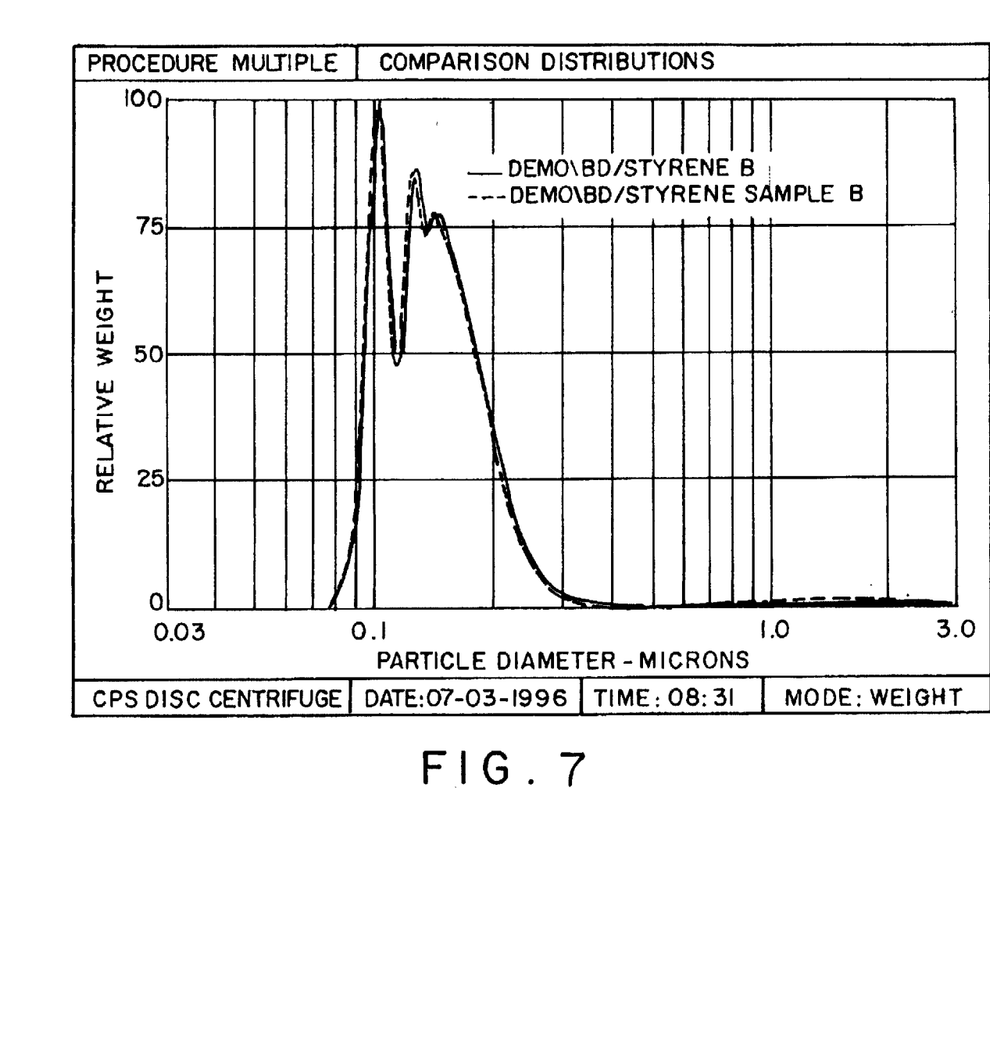
FIG. 7 is a chart showing the results of a styrene-butadiene copolymer latex analysis.

The contents of the syringe were injected into the "V" shaped groove at the start of the analysis, and distribution data was collected by measuring the attenuation of a light beam (470 nanometer wavelength) that passed through the disc approximately 8 millimeters above the bottom of the centrifuge chamber. The above analysis was repeated immediately after the completion of the first analysis, using the same density gradient and injection method. Each analysis (measuring down to 0.08 micron) required approximately 40 minutes. FIG. 7 is a chart showing the two distributions overlaid on the same graph. These distributions show the high resolving power and excellent repeatability that is typical of the DGSDS method. The series of peaks in the distributions reveal the extent of agglomeration in the latex sample: the smallest peak in the series (0.103 micron) is the parent distribution, while the larger peaks represent multiple agglomerates of the parent distribution: 2 particles=0.127 micron, 3 particles=0.143 micron. Larger agglomerates (4 or more particles) could not be resolved, and show in the distribution as a broad peak ranging from 0.16 to 0.32 micron.

EXAMPLE 2

Figure 8:
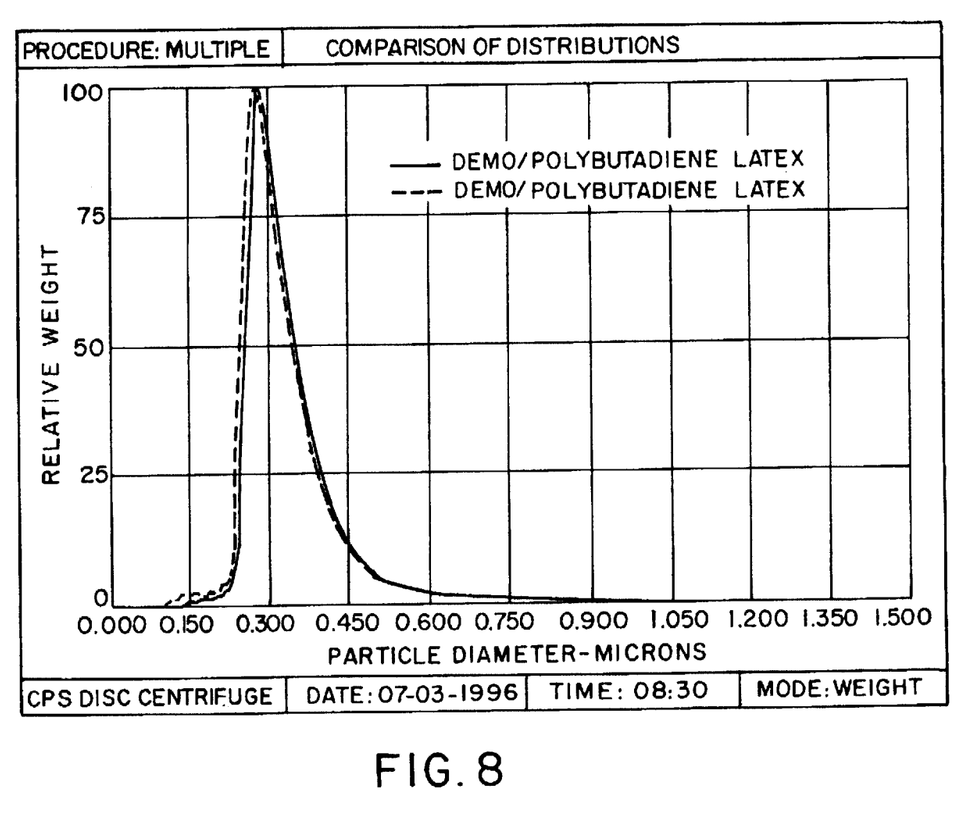
FIG. 8 is a chart showing the Comparison of Distribution of particles results from a polybutadiene latex analysis.

In FIG. 8 a chart shows the measurement of a sample of polybutadiene latex (particle density=0.89 g/ml) using the same conditions and technique as in Example 1, except water was substituted for deuterium oxide in the density gradient and sample dilution fluids. The analysis was run twice, with the second run immediately following the first. Each run required approximately 15 minutes to reach 0.15 micron. The results of the two analyses are shown in FIG. 8 as a direct overlay. The excellent repeatability of the method is evident from the virtually identical results of the two tests.

EXAMPLE 3

Figure 9:
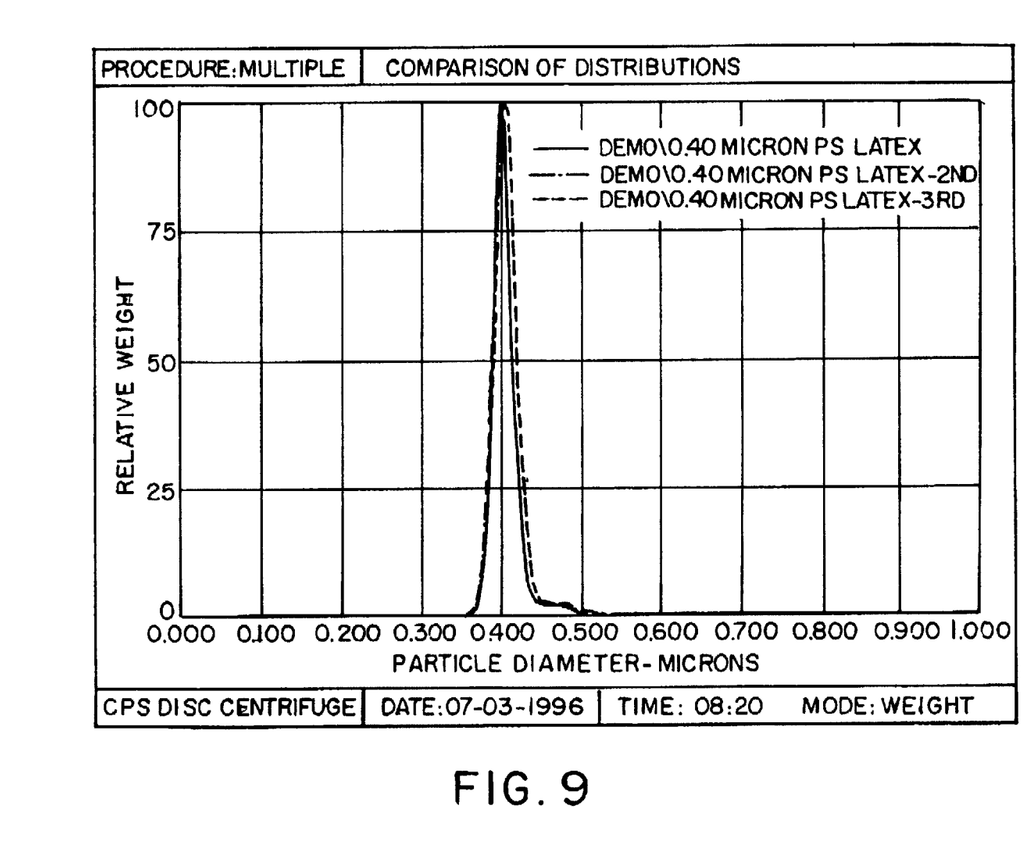
FIG. 9 is a chart showing the Comparison of Distribution of particles results from a polystyrene latex analysis.

FIG. 9 is a chart showing the measurement of a sample of narrow polystyrene latex (particle density=1.050 g/ml, 0.4 micron nominal size) using the same conditions and technique as Example 1, except that the disc was run at 10,000 RPM, and the concentration of the diluted sample was reduced to about 0.1% by weight polystyrene. The results of three replicate runs are shown as a direct overlay in FIG. 9. The excellent resolution of the method is evident from the distribution curves. Using a density gradient based on deuterium oxide along with this invention allows virtually any aqueous dispersion of particles to be accurately measured using DGSDS; particles with densities between about 0.95 and 1.05 g/ml can be measured using this invention along with deuterium oxide, particles less than 0.95 g/ml can be measured using this invention and either deuterium oxide or normal water, and particles more dense than 1.05 g/ml can be measured by conventional DGSDS.

Figure 5:
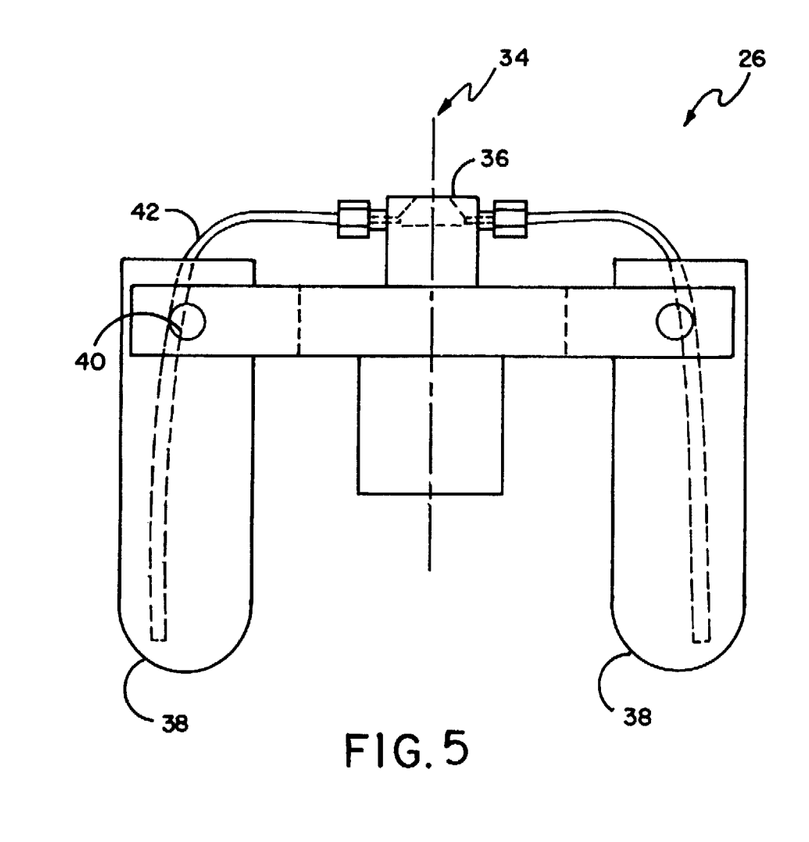
FIG. 5 illustrates a side cross-sectional view of a "swinging bucket" type centrifuge for use with the method of this invention.
Figure 5A:
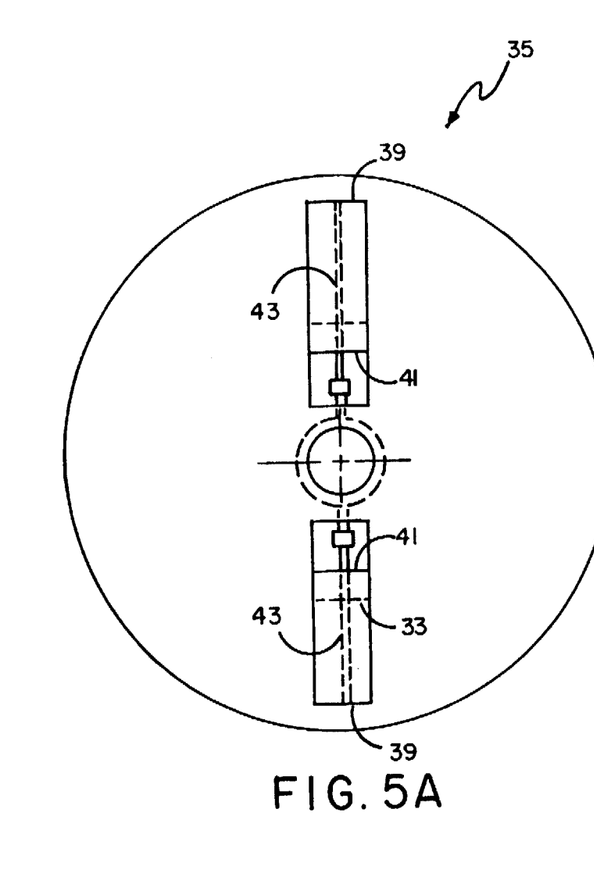
FIG. 5a illustrates a front view of a centrifuge of the segmented disc design.
Figure 5B:
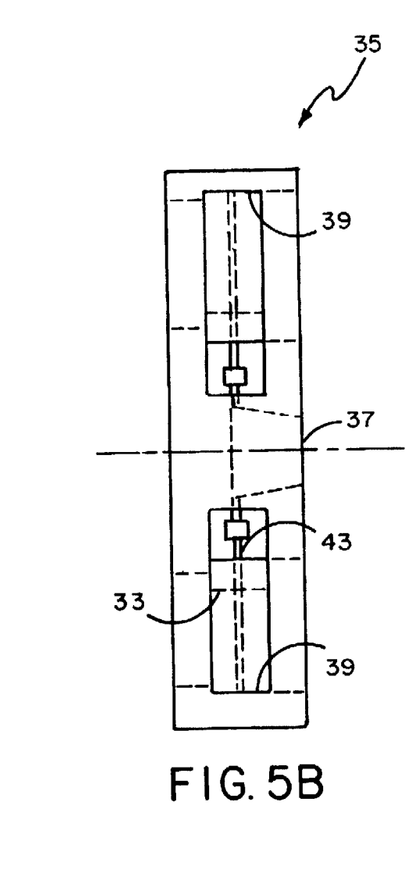

As mentioned above the method of this invention can be practiced in other types of centrifuges such as, for example, the swinging bucket centrifuge 26, illustrated in a side view in FIG. 5, wherein the axis of rotation 34 passes through groove 36 into which the sample can be placed which will pass through tubes 42 down to bottom 38 of each swinging bucket which swings out and pivots on pivots 40. FIG. 5a illustrates a front view of a segmented disc-type centrifuge 35. In the segmented disc centrifuge the cuvettes 41, which are usually made of glass and can be removed from the centrifuge for cleaning, contain liquid to a top level 33. Flexible capillary tubes 43 will carry the particle suspension from the central entry chamber 37, seen in FIG. 5b, down to the bottom 39 of each cuvette 41. In the segmented disc centrifuge the fluids to be entered into the cuvette can also be entered through the capillary tubes at the start of the operation in the reverse order of the desired density gradient, with the least dense fluid entered first. Once the fluids are entered into the cuvette, then the particle suspension sample to be tested can be entered through central entry chamber 37 to pass down capillary tubes 43 to the bottom 39 of each cuvette. Other modifications can be made to other types of centrifuges so as to allow the deposit of sample to be tested to be made in the bottom thereof so that the method of this invention can be practiced in other types of centrifuges.

If any air is entrained when a sample is injected at the base of the centrifuge chamber, such air can produce an injection artifact which is a relatively low amplitude broad peak of large diameter air bubbles that will pass the detector beam starting very shortly after the sample injection is made. While it is possible to simply ignore the injection artifact because it is usually very small compared to the rest of the distribution or to subtract mathematically from the final distribution, it is best to use an additional technique to minimize the quantity of any entrained air. When using this preferred embodiment of the method of this invention, the size of the air artifacts can be minimized by the following procedures. First the diameter of the capillary channels should be as small as practicable to minimize any air that might be contained in the channels between the base of the V-shaped groove and the equilibrium liquid level in the channels. Any air trapped when a sample injection is made can be carried by the sample to the bottom of the centrifuge chamber. Thus it is desirable for the top 64 of the liquid level in centrifuge chamber 22 to be reasonably close to the base 28 of the V-shaped groove to minimize the volume of air trapped in the capillary channels. Any sample should be injected into the V-shaped groove at an angle that allows the formation of a smooth film on one side of the "V" of the V-shaped groove to minimize the possibility of air entrainment due to foaming during the injection.

Figure 10:
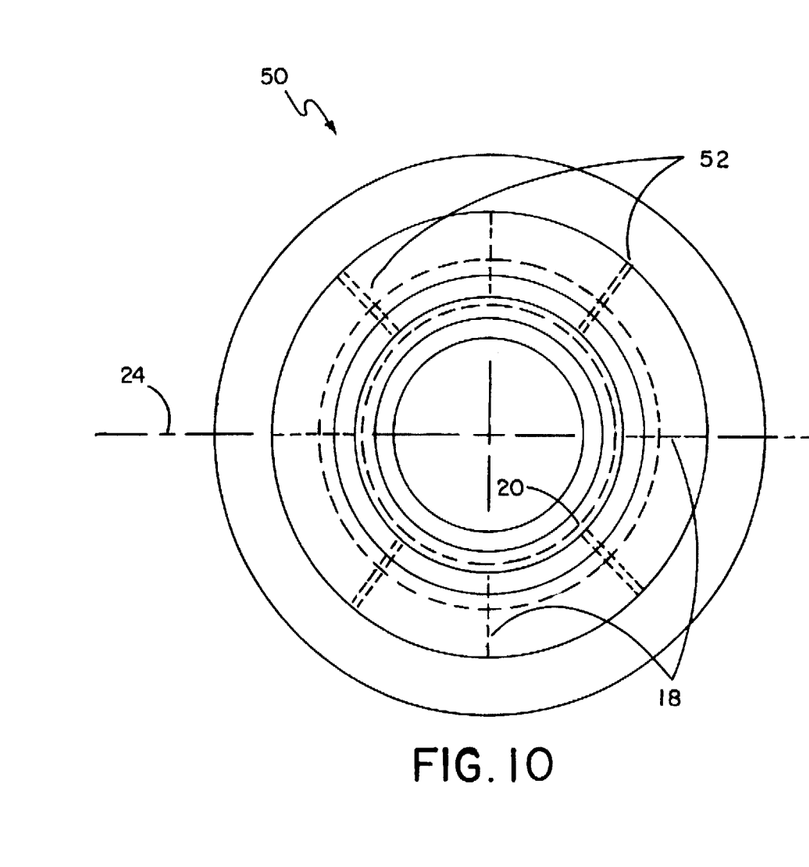
FIG. 10 illustrates a front view of a hollow-disc centrifuge chamber utilizing the V-groove structure of this invention and overflow system.
Figure 11:
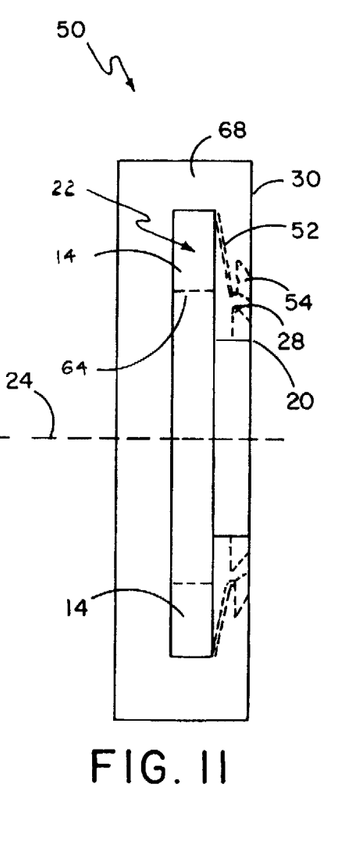
FIG. 11 illustrates a side cross-sectional view through the hollow-disc centrifuge chamber of FIG. 10.

The ideal liquid level in the centrifuge to minimize air entrainment is very slightly below base 28 of the V-shaped injection groove. However, each sample injection increases the total volume of fluid 14 in the disc, so if the initial level of top 64 of the fluid is close to base 28 of groove 20, then only a limited number of samples can be injected before the top 64 of the fluid level reaches base 28 of groove 20. The embodiments shown in FIGS. 10 and 11 have been designed to overcome this problem of air entrainment. Seen in FIG. 10 is a front view of hollow disc 50 with V-shaped groove 20 formed therein with four capillary channels 18 to direct the sample to the base of chamber 22. In this structure, also seen in the side view of FIG. 11, are additional capillary channels 52 which are formed to allow chamber 22 to overflow into holding basin 54 formed within front wall 30 of the disc just below V-shaped groove 20. Each time an injection is made into V-shaped chamber 20 and the fluid passes down through channels 18, an equal volume of liquid overflows through channels 52 into holding basin 54 so that the top 64 of the fluid in the chamber remains at a constant level. The location where overflow channels 52 connect with disc chamber 22 is not critical for controlling the liquid level, that is, any connection below top 64 of the liquid level is acceptable. However, a connection made near outside edge 68 of chamber 22 will minimize gradient disruption when used with high volume samples.

Another problem that has been addressed when using the method and structure of this invention is that of gradient disruption. Many samples have a high enough concentration that even a very small volume will give a strong detector response and a good signal to noise ratio. Typical samples are diluted to about 5,000 micrograms (of particles) per ml, and 20 microliters are injected, so the dry sample weight is typically in the range of 100 micrograms. However, some samples are extremely dilute (<20 micrograms per ml), so it may be necessary to inject a much larger sample volume to get an acceptable detector response. In some cases, sample volumes of 250 to 500 microliters are needed. Injection of a very small sample (<50 microliters) at the bottom of hollow disc centrifuge chamber has virtually no effect on the density gradient. However, a much larger sample volume can cause some transient mixing of different density layers in the centrifuge, because the injection of a large volume of liquid significantly reduces the radius of rotation of all the liquid in the disc. Before an injection is made, all of the fluid in the disc centrifuge has the same rotational speed as the disc itself. When a relatively large volume of liquid (250–500 microliters) is added quickly to the bottom of the chamber, the radius of rotation for all of the overlying liquid is quickly (<1 second) reduced by the thickness of the newly added liquid at the outside edge of the disc. This means that all of the overlying liquid suddenly rotates slightly faster than the disc; the linear velocity of the liquid cannot suddenly change, but its radius of rotation does suddenly change. The difference in speed between the disc and the liquid causes some temporary turbulence in the density gradient. This turbulence produces an injection artifact because the optical transmittance (and x-ray transmittance) of the fluid fluctuates rapidly during turbulent flow. The intensity of the detector beam therefore fluctuates, producing an injection artifact in the distribution. The optical transmittance of a pure fluid does not normally change due to turbulence, but the fluid in the disc is not uniform in composition and the density gradient varies in refractive index with composition, so turbulence causes rapid changes in refractive index and scattering of the detector beam.

The hollow disc design shown in FIGS. 10 and 11 minimizes the artifact from injection of a large sample by allowing a volume of liquid equal to the sample volume to exit the disc from a point near the bottom 62 of chamber 22. The larger diameter of the overflow capillary channels ensures that the resistance to fluid flow up overflow channels 52 is much less than the resistance of sample flow down the sample entry channels 18. This leveling of the fluid eliminates the possibility of a transient increase in the liquid level during the sample injection. Since there is no reduction in the radius of rotation in the overlying liquid, there is no tendency for turbulence and thus no injection artifact.

Although the present invention has been described with reference to particular embodiments, it will be apparent to those skilled in the art that variations and modifications can be substituted therefor without departing from the principles and spirit of the invention.

I claim:

1. A method for analysis of the size and/or distribution of low-density particles by centrifugal sedimentation in a centrifuge chamber having a bottom, a top, and an axis of rotation adjacent said top, said centrifuge chamber containing a fluid volume having a density gradient and an initial top level such that particles lower in density than the gradient densities of the fluid in said centrifuge chamber can move through the volume of the fluid, said method comprising the steps of:

spinning said centrifuge sedimentation chamber at the axis of rotation;

delivering said low-density particles to be analyzed as a suspension to said bottom of said spinning centrifuge chamber;

allowing said low-density particles in said delivered suspension to rise through said density gradient fluid from said bottom towards said top of said spinning centrifuge chamber; and providing means to analyze the size and/or distribution of said low-density particles as said particles rise in said gradient density fluid of said spinning centrifuge chamber.

2. The method of claim 1 further including the step of:

removing fluid from below said initial top level of said fluid in said centrifuge chamber after delivery of said particles to be analyzed for maintaining a constant fluid level at said initial top level in said centrifuge chamber.

3. The method of claim 1 further including, before the step of delivering said particles to the bottom of said centrifuge chamber, the step of:

initially suspending said particles in a fluid which is more dense than the density of the fluid at said bottom of said centrifuge chamber.

4. The method of claim 1 further including, before the step of delivering said particles to the bottom of said centrifuge chamber, the step of:

initially suspending said particles in a fluid which fluid is soluble in said fluid within said centrifuge chamber.

5. The method of claim 1 further including the step of:

providing a fluid in said centrifuge chamber that is at least 0.02 gm/ml more dense than the density of the particles to be analyzed.

6. The method of claim 1 further including the step of:

avoiding the entrapment of air during the step of delivering the particle suspension to said bottom of said centrifuge chamber.

* * * * *